US009518294B2

(12) United States Patent
Luan et al.

(10) Patent No.: US 9,518,294 B2
(45) Date of Patent: *Dec. 13, 2016

(54) BASE-BY-BASE RATCHETING OF DNA/RNA IN A Y-SHAPED NANOCHANNEL

(71) Applicant: International Business Machines Corporation, Armonk, NY (US)

(72) Inventors: Binquan Luan, Chappaqua, NY (US); Ruhong Zhou, Stormville, NY (US)

(73) Assignee: International Business Machines Corporation, Armonk, NY (US)

( * ) Notice: Subject to any disclaimer, the term of this patent is extended or adjusted under 35 U.S.C. 154(b) by 125 days.

This patent is subject to a terminal disclaimer.

(21) Appl. No.: 14/615,924

(22) Filed: Feb. 6, 2015

(65) Prior Publication Data

US 2015/0159209 A1    Jun. 11, 2015

Related U.S. Application Data

(60) Division of application No. 13/971,486, filed on Aug. 20, 2013, which is a continuation of application No. 13/724,041, filed on Dec. 21, 2012.

(51) Int. Cl.
| | | |
|---|---|---|
| *C12Q 1/68* | (2006.01) | |
| *G01N 27/447* | (2006.01) | |
| *G01N 27/453* | (2006.01) | |
| *B82Y 30/00* | (2011.01) | |
| *B82Y 5/00* | (2011.01) | |

(52) U.S. Cl.
CPC ............ *C12Q 1/6869* (2013.01); *G01N 27/447* (2013.01); *G01N 27/44791* (2013.01); *G01N 27/453* (2013.01); *B82Y 5/00* (2013.01); *B82Y 30/00* (2013.01); *Y10S 977/742* (2013.01); *Y10S 977/781* (2013.01); *Y10S 977/924* (2013.01)

(58) Field of Classification Search
None
See application file for complete search history.

(56) References Cited

U.S. PATENT DOCUMENTS

| | | |
|---|---|---|
| 7,144,563 B2 | 12/2006 | Rao et al. |
| 7,696,505 B2 | 4/2010 | Hyde et al. |
| 2002/0187503 A1 | 12/2002 | Harrold et al. |
| 2007/0125946 A1 | 6/2007 | Boye et al. |
| 2007/0194225 A1 | 8/2007 | Zorn |
| 2008/0242556 A1* | 10/2008 | Cao ............... B01L 3/502761 506/9 |
| 2011/0162966 A1 | 7/2011 | Burke et al. |
| 2011/0236984 A1 | 9/2011 | Sun et al. |
| 2012/0160687 A1 | 6/2012 | Akeson et al. |

FOREIGN PATENT DOCUMENTS

CN    101765462 A    6/2010

OTHER PUBLICATIONS

Stuart Lindsay, et al.; Carbon Nanotubes Show Promise for High-Speed Genetic Sequencing (w/video); retrieved on Feb. 17, 2016 from http//phys.rog/news/2009-12-carbon-nanotubes-high-speed-genetic-sequencing.html; Phys.org; p. 1-3; Dec. 31, 2009.
Tracy Vence; "Carbon Nanotubes Could Increase DNA Sequencing"; Biotechniques; Retrieved on Mar. 28, 2016 from http://www.biotechniques.com/news/Carbon-nanotubes-could-increase-DNA-sequencing-control/biotechniques-186289.html; 1 page; Jan. 12, 2010.
Zaraska, Leszek, et al; "Porous Alumina Membranes with Branched Nanopores as Templates for Fabrication of Y-Shaped Nanowire Arrays"; J. Solid State Electrochem; vol. 16; p. 3611-3619; 2012.
Deepak et al., "Synthetic Strategies for Y-Junction Carbon Nanotubes," Chemical Physics Letters 345 (2001) 5-10; Sep. 7, 2001; www.elsevier.com/locate/cplett; 6 pages.
Liu et al., "Translocation of Single-Stranded DNA Through Single-Walled Carbon Nanotubes," Science, www.sciencemag.org, vol. 327, Jan. 1, 2010; 4 pages.
Luan et al., "Base-By-Base Ratcheting of Single Stranded DNA through a Solid-State Nanopore," The American Physical Society, Physical Review Letters, week ending Jun. 11, 2010; PRL 104, 238103 (2010); 4 pages.
Lulevich et al., "Frictionless Sliding of Single-Stranded DNA in a Carbon Nanotube Pore Observed by Single Molecule Force Spectroscopy," Nano Letters, 2011, 11, 1171-1176; 6 pages.
Papadopoulos et al., "Electronic Transport in Y-Junction Carbon Nanotubes," Physical Review Letters, vol. 85, No. 16, Oct. 16, 2000; 4 pages.
Tsutsui et al., "Identifying Single Nucleotides by Tunnelling Current," Nature Nanotechnology, Letters, Published Online: Mar. 21, 2010; DOI: 10.1038/NNANO.2010.42; 5 pages.
Tu et al., "Water-Mediated Signal Multiplication with Y-Shaped Carbon Nanotubes," PNAS, Oct. 27, 2009, vol. 106, No. 43, 18120-18124; www.pnas.org/cgi/doi/10.1073/pnas.0902676106; 5 pages.
Wang et al., "Cooperative Translocation Dynamics of Biopolymer Chains Though Nanopores in a Membrane: Slow Dynamics Limit," The European Physical Journal, Eur. Phys. J. E 33, 251-258 (2010); 8 pages.
Xie et al., "Electric Field-Induced Translocation of Single-Stranded DNA through a Polarized Carbon Nanotube Membrane," The Journal of Chemical Physics 127, 225101 (2007); 8 pages.

\* cited by examiner

*Primary Examiner* — Aaron Priest
(74) *Attorney, Agent, or Firm* — Cantor Colburn LLP; Vazken Alexanian (57) ABSTRACT

A mechanism is provided for ratcheting a double strand molecule. The double strand molecule is driven into a Y-channel of a membrane by a first voltage pulse. The Y-channel includes a stem and branches, and the branches are connected to the stem at a junction. The double strand molecule is slowed at the junction of the Y-channel based on the first voltage pulse being weaker than a force required to break a base pair of the double strand molecule. The double strand molecule is split into a first single strand and a second single strand by driving the double strand molecule into the junction of the Y-channel at a second voltage pulse.

5 Claims, 7 Drawing Sheets

→ Driving the double strand molecule into a Y-channel of a membrane by a first voltage pulse, the Y-channel comprises a stem and branches, the branches being connected to the stem at a junction  505

→ Slow the double strand molecule at the junction of the Y-channel based on the first voltage pulse being weaker than a force required to break a base pair of the double strand molecule  510

→ Splitting the double strand molecule into a first single strand and a second single strand by driving the double strand molecule into the junction of the Y-channel at a second voltage pulse  515

BASE-BY-BASE RATCHETING OF DNA/RNA IN A Y-SHAPED NANOCHANNEL

DOMESTIC PRIORITY

The present application is a divisional of U.S. patent application Ser. No. 13/971,486, filed Aug. 20, 2013, which is a continuation of U.S. patent application Ser. No. 13/724,041, filed on Dec. 21, 2012, the contents of each application are incorporated by reference herein.

BACKGROUND

The present invention relates to nanopore/nanochannel devices, and more specifically, to capture and control of molecules in nanopore/nanochannel devices.

Nanopore sequencing is a method for determining the order in which nucleotides occur on a strand of deoxyribonucleic acid (DNA). A nanopore (also referred to a pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to an embodiment, a method for ratcheting a double strand molecule is provided. The method includes driving the double strand molecule into a Y-channel of a membrane by a first voltage pulse. The Y-channel includes a stem and branches, and the branches are connected to the stem at a junction. The method includes slowing the double strand molecule at the junction of the Y-channel based on the first voltage pulse being weaker than a force required to break a base pair of the double strand molecule, and splitting the double strand molecule into a first single strand and a second single strand by driving the double strand molecule into the junction of the Y-channel at a second voltage pulse.

According to an embodiment, a system for ratcheting a double strand molecule is provided. The system includes a membrane with a Y-channel, and the Y-channel includes a stem and branches, where the branches are connected to the stem at a junction. The system includes a top fluidic chamber on one side of the membrane and a bottom fluidic chamber on an opposing side of the membrane. A first voltage pulse of a voltage source drives the double strand molecule into the Y-channel of the membrane. The double strand molecule is slowed at the junction of the Y-channel based on the first voltage pulse being weaker than a force required to break a base pair of the double strand molecule. A second voltage pulse of the voltage source drives the double strand molecule into the junction of the Y-channel to split the double strand molecule into a first single strand and a second single strand.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Sequencing DNA at an affordable cost has inspired many new DNA sequencing methods. However, one existing technical challenge is to control the motion of DNA at a single-nucleotide resolution. Without such control, some nucleotides could be read multiple times while some others could be missed during a sequencing process. Therefore, it is desirable to have a device that can nucleotide-by-nucleotide (i.e., base-by-base) ratchet DNA. Nature has built a small yet efficient DNA-ratcheting machine: DNA polymerase is a protein molecule which controls a directional motion of DNA nucleotide-by-nucleotide. DNA polymerase is used in a sequencing technology based on an existing method. To mimic the ratcheting process by the DNA polymerase, a man-made DNA-ratcheting machine is provided herein using synthetic nanomaterials. According to an embodiment, a nanodevice has a Y-shaped nanochannel (e.g., a Y-channel) to electrically drive a double-stranded DNA (dsDNA) into the stem channel, followed by electrically unzipping of the dsDNA and threading each single-stranded DNA (ssDNA) through a branch channel.

Figure 1:
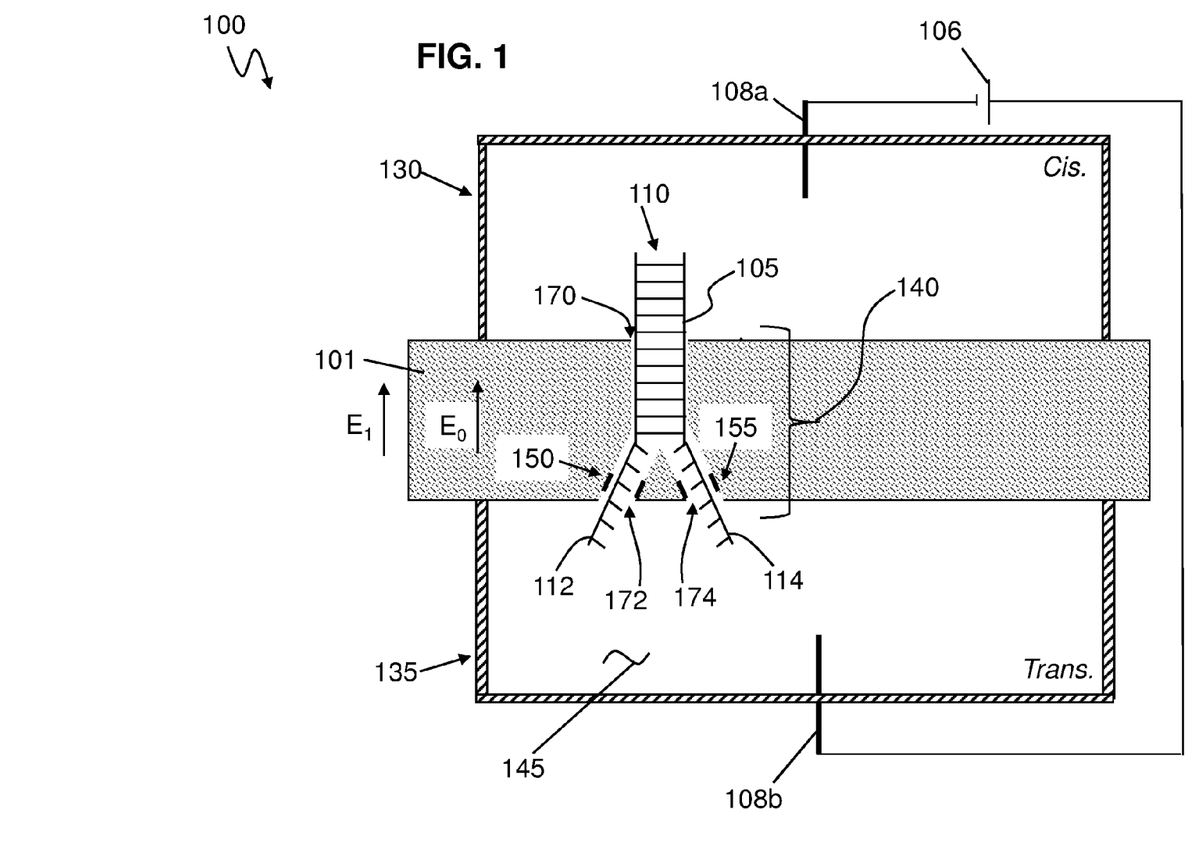
FIG. 1 is a cross-sectional view of a DNA-ratcheting nanodevice according to an embodiment.

Now turning to the figures, FIG. 1 is a cross-sectional view of a DNA-ratcheting nanodevice 100 according to an embodiment. A Y-channel 140 is embedded in a membrane 101, and the Y-channel 140 is a Y-shaped nanochannel. A double strand DNA molecule (dsDNA) 110 is being driven through and unzipped in the Y-channel 140 as discussed further herein. The membrane 101 may be a solid state membrane, such as, e.g., $SiO_2$, $Si_3N_4$, and/or another insulating material. The membrane 101 may have a thickness of 100 nm. Generally, a channel can be a nanopore through a solid membrane or a surface channel in a typical nanofluidic device (such as a lab-on-chip) as understood by one skilled in the art.

One kind of Y-channel 140 is the Y-shaped carbon nanotube (Y-CNT) as shown in FIG. 1. Several methods have been developed to fabricate Y-shaped CNTs which have been designed to transfer and multiply charge signals at molecular level (molecular signal transduction).

Further information regarding Y-shaped carbon nanotubes is discussed in the following articles which are herein incorporated by reference: Papadopoulos C, Rakitin A, Li J, Vedeneev A S, Xu J M (2000) Electronic transport in Y-junction carbon nanotubes. *Phys Rev Lett* 85:3476. Deepak F L, Govindaraj A, Rao C N R (2001) Synthetic strategies for Y-junction carbon nanotubes. *Chem Phys Lett* 345:5-10. Tu Y, Xiu P, Wan R, Hu J, Zhou R H, and Fang H P (2009), Water-mediated signal multiplication with Y-shaped carbon nanotubes, Proc. Natl. Acad. Sci. 106, 18120-18124.

In the DNA-ratcheting nanodevice 100, two fluidic chambers (cis. and trans.) 130 and 135 are separated by the solid membrane 101 and connected to one another by the Y-channel 140. The top fluidic chamber 130, the bottom fluidic channel 135, and the Y-channel 140 are all filled with an electrically conductive solution 145. The electrically conductive solution 145 is an electrolyte solution as understand by one skilled in the art.

Figure 2:
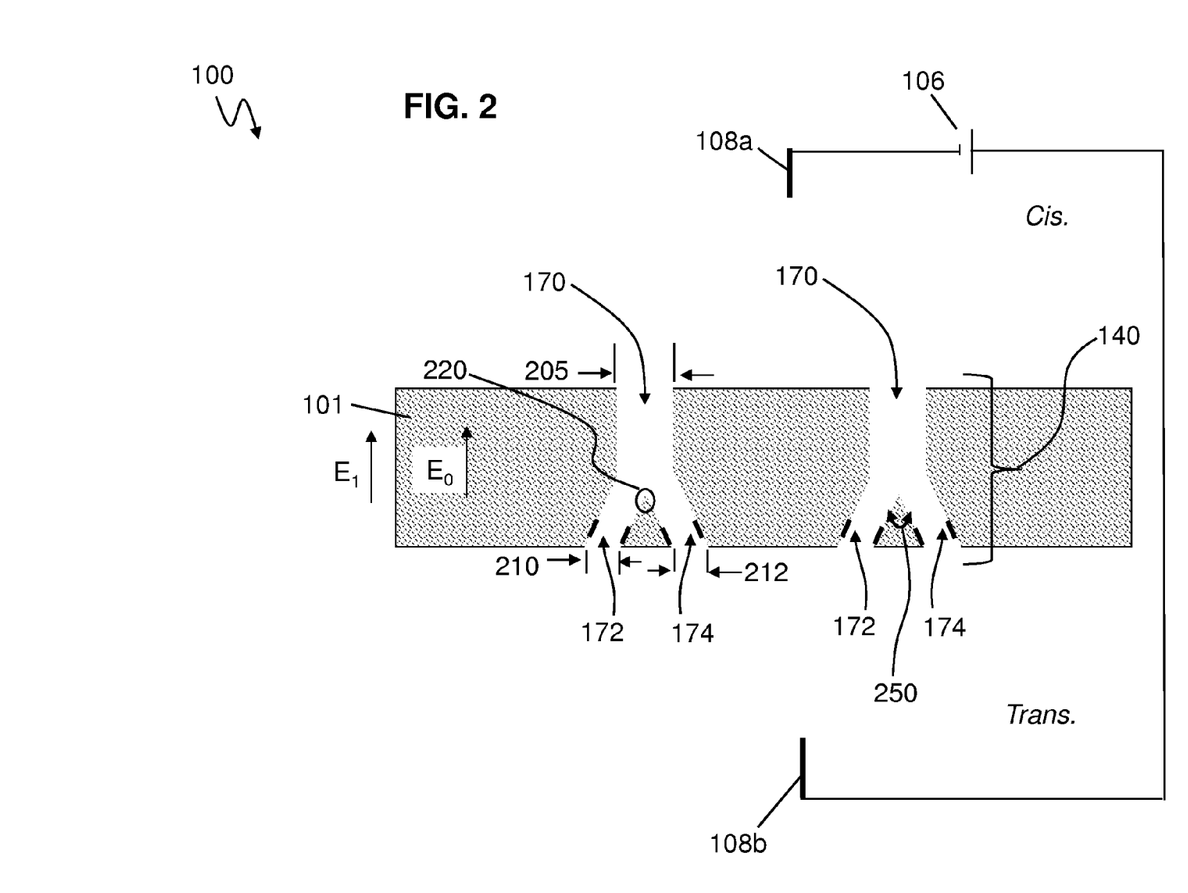
FIG. 2 is an abbreviated version of the nanodevice in which a membrane includes two Y-channels according to an embodiment.

The Y-channel 140 (Y-CNT) has a stem 170 connected to left branch 172 and right branch 174. FIG. 2 illustrates an abbreviated version of the nanodevice 100 in which the membrane 101 includes two Y-channels 140. It is noted that multiple Y-channels 140 may be formed in the membrane 101.

Although understood to be present, FIG. 2 shows the nanodevice 100 without the double strand DNA molecule 110 and the fluidic chambers 130 and 135 so as not to obscure the figure. Example dimensions of the Y-channel 140 are provided below. The stem 170 may have a width 205 (and/or diameter) of 4 to 10 nm (nanometers) and/or sub ten nanometers. The left branch 172 may have a width 210 (and/or diameter) of 2 to 4 nm and/or sub 5 nanometers. The right branch 174 may have a width 212 (and/or diameter) of 2 to 4 nm and/or sub 5 nanometers. The angle 250 of a junction 220 may be 30 to 120 degrees, to form the left and right branches 172 and 174.

With reference to FIG. 1, a voltage source 106 is connected to electrode 108a in the top fluidic chamber 130 and connected to electrode 108b in the bottom fluidic chamber 135. The voltage source 106 (along with ammeters 160 and 165 in FIG. 4) may be implemented in and/or controlled by a computer test setup 700 discussed in FIG. 7. Voltage pulse $V_0$ of the voltage source 106 is applied to the electrodes 108a and 108b which results in a biasing electric field $E_0$ being applied across the membrane 101, by inserting the two electrodes 108a and 108b into cis. and trans. chambers, respectively. The electrodes 108a and 108b may be Ag/AgCl electrodes connected to a battery or any direct current voltage source (e.g., the voltage source 106).

The (negatively charged) dsDNA molecule 110 can be electrophoretically driven into the stem 170 of the solid-state Y-channel 140 by the voltage pulse $V_0$ applied by the voltage source 106. When the dsDNA molecule 110 arrives at the junction 220 (shown in FIG. 2) of the Y-channel 140, a higher biasing electric field $E_1$ (i.e., a higher voltage pulse $V_1$ is applied by the voltage source 106) is utilized to overcome the energy barrier for unzipping one base-pair of the dsDNA molecule 110, for breaking two base-stacking, and for rotating the dsDNA segment by 36 degree (the angle between neighboring base-pairs in dsDNA). Particularly, the higher voltage pulse $V_1$ (resulting in the higher electric field $E_1$) breaks the dsDNA molecule 110 into ssDNA 112 in the left branch 172 and into ssDNA 114 in the right branch 174 of the Y-channel 140, when the dsDNA molecule 110 is driven (forced) into the sharp end of the junction 220.

Accordingly, once the dsDNA molecule 110 is driven through the stem 170 to the junction 220 by the electric field $E_0$ (via the voltage pulse $V_0$), the dsDNA molecule 110 (temporarily) stops (or slows) at the junction 220. Then, the higher electric field $E_1$ (via the voltage pulse $V_1$) is applied, which is strong enough to break (i.e., overcome the energy barrier for unzipping) the base pair of the dsDNA molecule 110 that is positioned at (abuts) the junction 220. After the voltage pulse $V_1$ is applied by the voltage source 106 while the dsDNA molecule 110 abuts the junction 220, the dsDNA molecule 110 unzips (i.e., the base pair is broken) into the ssDNA molecule 112 and ssDNA molecule 114 respectively in branches 172 and 174. The ssDNA molecule 112 has a chain of single bases (connected by a DNA backbone), and the ssDNA molecule 114 has a chain of single bases (connected by a DNA backbone), as understood by one skilled in the art.

Figure 3:
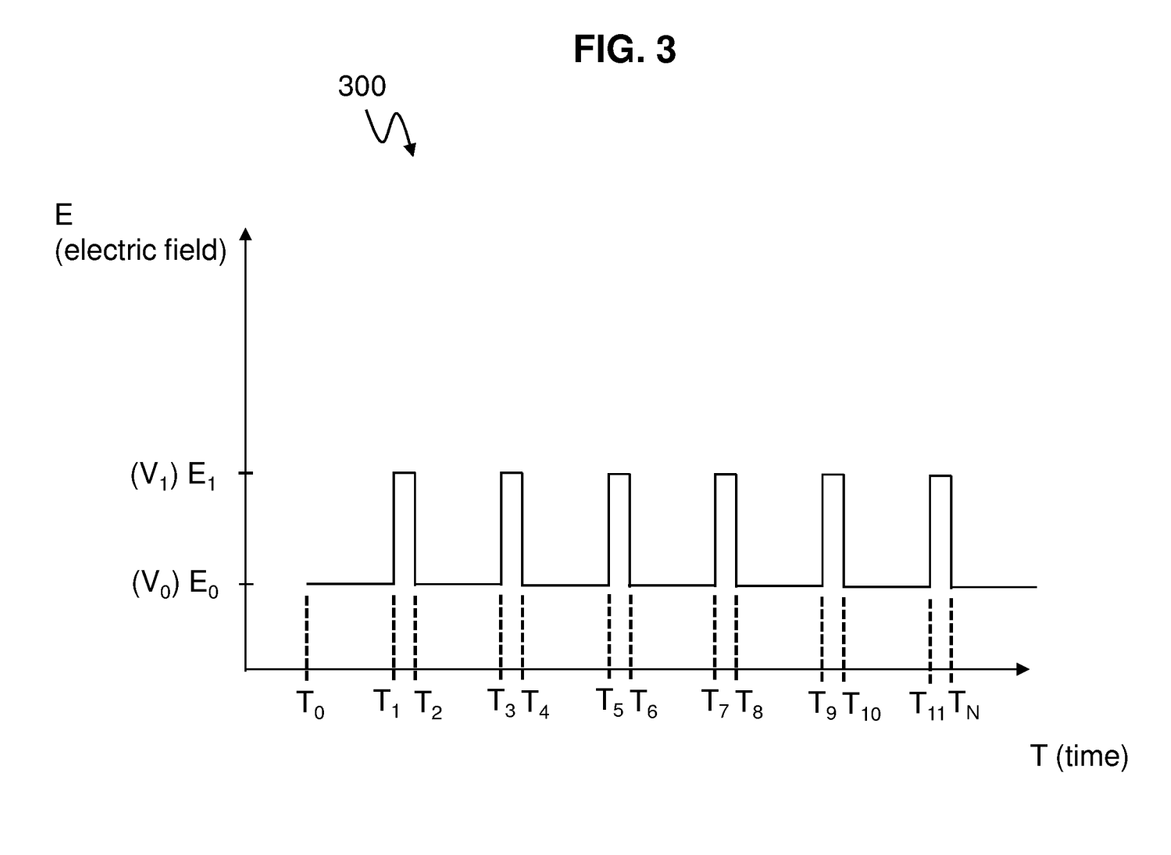
FIG. 3 illustrates a time-dependent biasing electric field chart to ratchet a DNA molecule through the Y-channel according to an embodiment.

FIG. 3 illustrates a time-dependent biasing electric field chart 300 to ratchet the DNA molecule 110 through the Y-channel 140 according to an embodiment. The y-axis shows the electric field E, and the x-axis shows the time T.

As discussed herein, driving voltage pulse $V_0$ is applied by the voltage source 106 to drive (i.e., move) the dsDNA molecule 110 from the top fluidic chamber 130 into the Y-channel 140, though the stem 170, and to the junction 220 (i.e., temporarily stopping at the junction 220 because the electric field $E_0$ is not strong enough to break the base pair abutting the tip of the junction 220). For example, the chart 300 shows that the electric field $E_0$ (via driving voltage pulse $V_0$) is applied for time $T_0$ through $T_1$. Then, the higher voltage pulse $V_1$ is applied for time $T_1$ through $T_2$ resulting in higher electric field $E_1$, as shown in FIG. 3. Once the higher electric field $E_1$ breaks (i.e., unzips) the base pair that was previously positioned at the junction 220, the driving voltage pulse $V_0$ is again applied (for time $T_2$ through $T_3$) to drive (i.e., advance) the dsDNA molecule 110 to position (i.e., stop) the next base pair at the junction 220. The higher voltage pulse $V_1$ is again needed (and applied via voltage source 106 for time $T_3$ through $T_4$) to break this next base pair now positioned at the junction 220. This process repeats to ratchet the dsDNA molecule 110 through the Y-channel 140 one base (i.e., one nucleotide spacing) at a time, and results in the dsDNA molecule 110 being unzipped into the ssDNA molecule 112 and ssDNA molecule 114.

As shown in FIG. 3, a pulse with a higher electric field $E_1$ is applied to open one base-pair and thread two complimentary nucleotides into two branches respectively. By alternatingly applying the lower driving voltage pulse $V_0$ and the (base pair breaking) higher voltage pulse $V_1$, FIG. 1 shows how the two ssDNA strands 112 and 114 are in two branches 172 and 174 of the Y-channel 140 and shows the remaining dsDNA molecule 105 is in the stem 170 of the Y-channel 140. Each time the high voltage pulse $V_1$ is applied, the DNA molecule 110 moves forward by one nucleotide (i.e., by one base), and this is the nucleotide-by-nucleotide ratcheting. Note that motion of ssDNA in a CNT can be frictionless. Therefore, each ssDNA 112 and 114 can be easily driven by an electric field through the Y-CNT (140). It is noted that when turning off the biasing electric field (i.e., turning off the voltage source 106), hybridizing of two complementary ssDNA molecules 112 and 114 occurs resulting in reverse ratcheting. For example, the dsDNA molecule 110 moves in reverse which is back into the top fluidic chamber 130, when the voltage source 106 is turned off, and the again forms base pairs.

As one example, the energy required to break the hydrogen bond between the base pair of the dsDNA molecule 110 (at the junction 220) is about 2-3 $k_B T$, where $k_B$ is the Boltzmann constant and T is the temperature.

An example driving voltage pulse $V_0$ to drive the dsDNA molecule 110 through the Y-channel 140 may be 0.1 volt, which results in the electric field $E_0$ and a downward driving force. The downward driving force (from cis. to trans.) does not break/unzip the base pair. The higher breaking voltage pulse $V_1$ may be 0.2 volts, applied for approximately 0.1 μs (micro-seconds).

Figure 4:
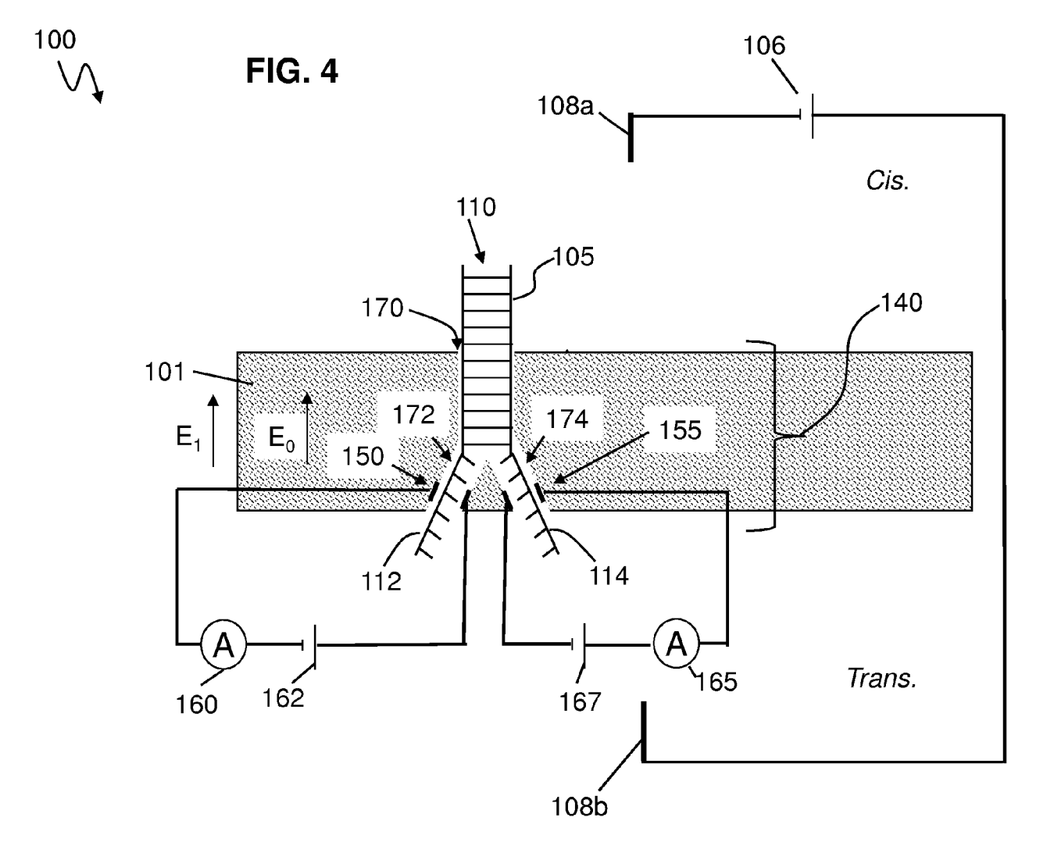
FIG. 4 is an abbreviated version of the nanodevice with sensors in the left and right branches to respectively sequence single strand DNA molecules according to an embodiment.

When one (or both) of the ssDNA molecules 112 and 114 exits a channel branch (e.g., respective branch 172 and/or 174) and enters the bottom fluidic chamber 135, a sensor (e.g., pair of electrodes 150 as one sensor and a pair of electrodes 155 as another sensor) built on the solid surface of the membrane 101 and at the end of a channel branch (e.g., branches 172 and/or 174) can be used to detect/read each base in the ssDNA molecule 112 and/or ssDNA molecule 114. FIG. 4 illustrates the nanodevice 100 with sensors in the left branch 172 and the right branch 174 to respectively sequence the ssDNA molecule 112 and the ssDNA molecule 114 according to an embodiment. FIG. 4 is one example of how the single strands may be sequenced and other sequencing methods may be utilized to read bases of the single strands, as understood by one skilled in the art.

For example, a sensor can consist of the pair of electrodes 150 in the left branch 172, and when a DNA base is in the gap of these two electrodes 150, an ammeter 160 can measure the base-sensitive tunneling current when voltage of the voltage source 162 is applied. To increase the reading accuracy and efficiency, the nanodevice 100 can be used to sequence two complementary ssDNA strands 112 and 114 simultaneously in the DNA ratcheting machine 100, which is another benefit of the current design. For example, the base between the pair of electrodes 150 (or maybe the previous or subsequent base) may be complementary to the base (concurrently) between the pair of electrodes 155, and the complementary bases can be respectively sequenced via respective voltages sources 162 and 167 and respective ammeters 160 and 165.

For example, while the voltage source 162 applies voltage to the pair of electrodes 150 and while the voltage source 167 applies voltage to the pair of electrodes 155, the ammeter 160 measures the tunneling current through the base (of the ssDNA 112) in the gap between electrodes 150 in the branch 172, and the ammeter 165 measures the tunneling current through the complementary base (of the ssDNA 114) in the gap between electrodes 155 in the branch 174. Accordingly, the two complementary DNA strands 112 and 114 are simultaneously or near simultaneously sequenced while the dsDNA molecule 110 is being ratcheted as discussed herein. This helps to confirm the accuracy of the bases being read in FIG. 4 because the respective bases in branches 172 and 174 should be complementary.

Complementary is a property shared between two nucleic acid sequences, such that when they are aligned antiparallel to each other, the nucleotide bases at each position will be complementary. Two bases are complementary if they form base pairs. For DNA, adenine (A) bases complement thymine (T) bases and vice versa; guanine (G) bases complement cytosine (C) bases and vice versa. With RNA, it is the same except that uracil is present in place of thymine, and therefore adenine (A) bases complement uracil (U) bases.

Figure 5:
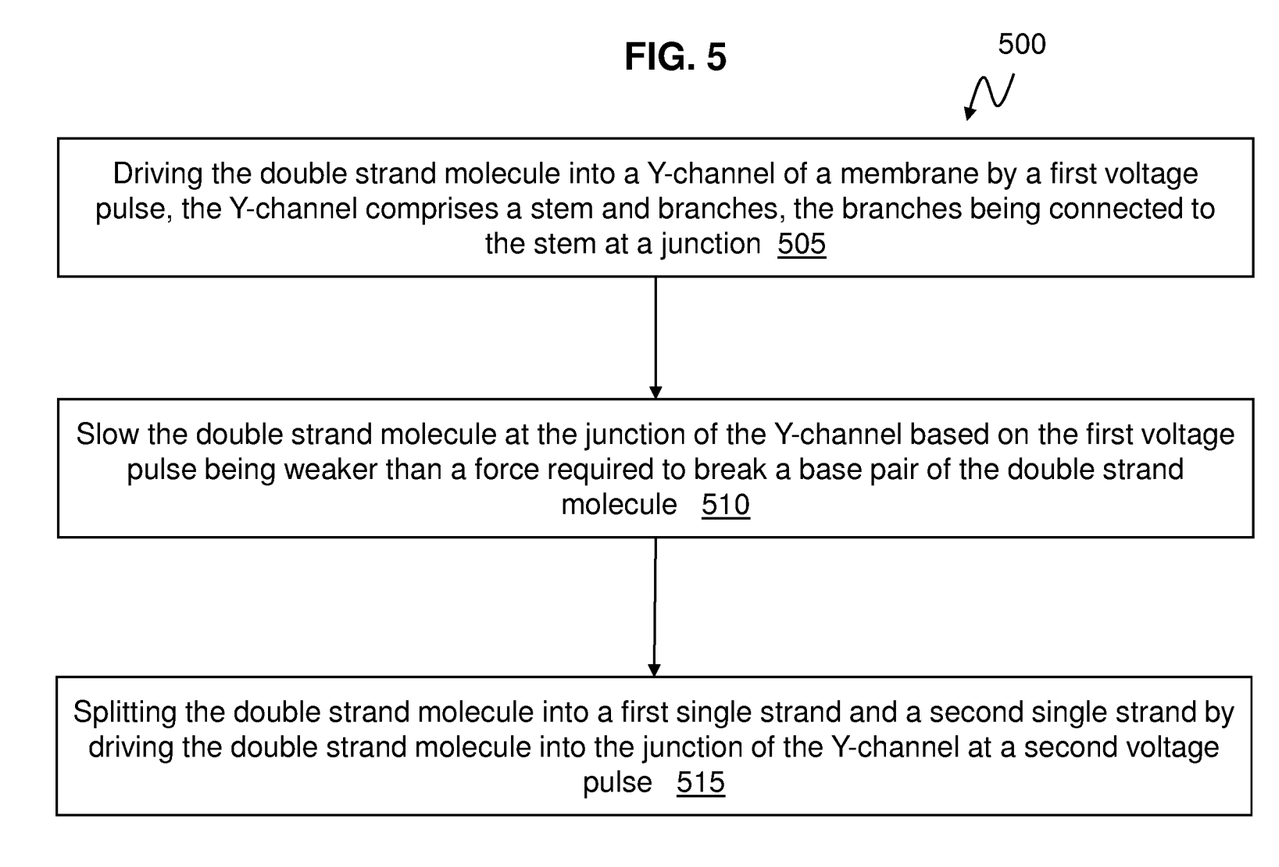
FIG. 5 is a method of ratcheting a double strand molecule through a Y-channel according to an embodiment.

FIG. 5 is a method 500 for ratcheting a double strand molecule (e.g., the dsDNA 110) through a Y-channel according to an embodiment. Reference can be made to FIGS. 1-4, 6, and 7. Various example may be for DNA but equally apply to RNA The voltage source 106 (e.g., computer test setup 700) is configured (or controlled) to drive the double strand molecule 110 into a Y-channel 140 in a membrane 101 by a first voltage pulse ($V_0$) at block 505. The Y-channel 140 comprises the stem 170 and branches 172 and 174, and the branches 172 and 174 connect to the stem at the junction 220.

The voltage source 106 (e.g., computer test setup 700) is configured (or controlled) to slow the double strand molecule 110 at the junction 220 of the Y-channel 140 based on the first voltage pulse ($V_0$) being weaker than the force required to break a base pair of the double strand molecule 110 at block 510.

The voltage source 106 (e.g., computer test setup 700) is configured (or controlled) to split the double strand molecule 110 into the first single strand 112 and the second single strand 114 by driving the double strand molecule 110 into the junction 220 of the Y-channel 140 at a second voltage pulse ($V_1$) at block 515.

The method further includes sequencing the first single strand (e.g., ssDNA 112) one (e.g., left branch 172) of the branches, and sequencing the second single strand (ssDNA 114) in another one (e.g., right branch 174) of the branches. Sequencing the first single strand in the one of the branches comprises reading one base in the first single strand, and sequencing the second single strand in the other one of the branches comprises reading another base of the second single strand, where one base (between the pair of electrodes 150) on the first single strand (ssDNA 112) is complimentary to the other base (between the pair of electrodes 155) on the second single strand.

The method further includes simultaneously sequencing complementary bases of the first single strand and the second single strand respectively in the branches 172 and 174.

Figure 6:
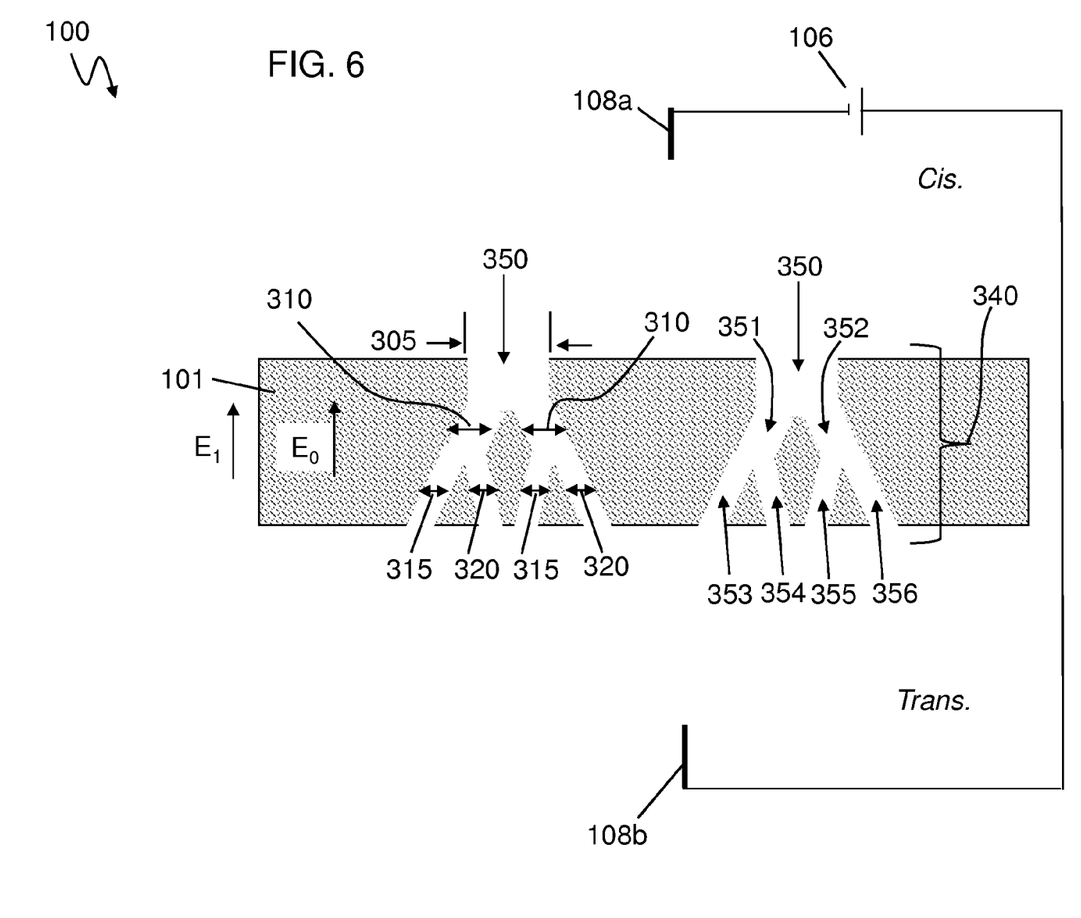
FIG. 6 is an abbreviated version of the nanodevice in which the membrane has Y-channels with multiple branches according to an embodiment.

The membrane 101 can include a plurality of Y-channels 140 (and/or Y-channels 340 in any combination), each having a stem and branches such as shown in FIGS. 2 and 6. The Y-channel 140 (340) is a Y-shaped carbon nanotube.

The voltage source 106 is configured to (automatically, semi-automatically, and/or manually) alternatingly apply the first voltage pulse ($V_0$) for a first time period (e.g., time $T_0$ through $T_1$) and the second voltage pulse ($V_1$) for a second time period (e.g., time $T_1$ through $T_2$) until the double strand molecule 110 has been completely split into the first single strand (ssDNA 112) and the second single strand (ssDNA 114). The direction of the double strand molecule can be reversed (i.e., going from bottom fluidic chamber 135 to top fluidic chamber 130 (trans. to cis.)) through the membrane 101 by discontinuing (both) the first voltage pulse and the second voltage pulse applied by the voltage source 106.

FIG. 6 is an abbreviated version of the nanodevice 100 in which the membrane 101 comprises Y-channels 340 with multiple branches according to an embodiment. The Y-channel 340 has stem 350 a main left branch 351 and a main right branch 352. The main left branch 351 splits into a secondary left branch 353 and a secondary right branch 354. Similarly, the main right branch 352 splits into a secondary left branch 355 and a secondary right branch 356.

The following are example dimensions of the Y-channel 340. The stem 350 may have a width 305 (and/or diameter) of 5 nm. The main left branch 351 and the main right branch 352 may each have a width 310 (and/or diameter) of 3.2 nm.

The secondary left branch 353 and the secondary left branch 355 may each have a width 315 (and/or diameter) of 2 nm.

The secondary right branch 354 and the secondary right branch 356 may each have a width 320 (and/or diameter) of 2 nm.

Although not shown so as not to obscure the figure, the branches 353, 354, 355, and 356 may each have its own sensor (i.e., electrode pair connected to a voltage source and ammeter) for reading the single bases.

As the stem 350 of Y-channels 340 is made large enough for dsDNA 110 to get in, the dsDNA 110 may go through either main left branch 351 or main right branch 352. If the dsDNA 110 enters main left branch 351, the ratcheting of dsDNA 110 occurs at the junction of the channels for the secondary left branch 353 and secondary right branch 354. Two DNA strands will be unzipped, and a single strand enters secondary left branch 353 and the complementary single strand enters secondary right branch 354, respectively (as discussed above in FIGS. 1-5).

Figure 7:
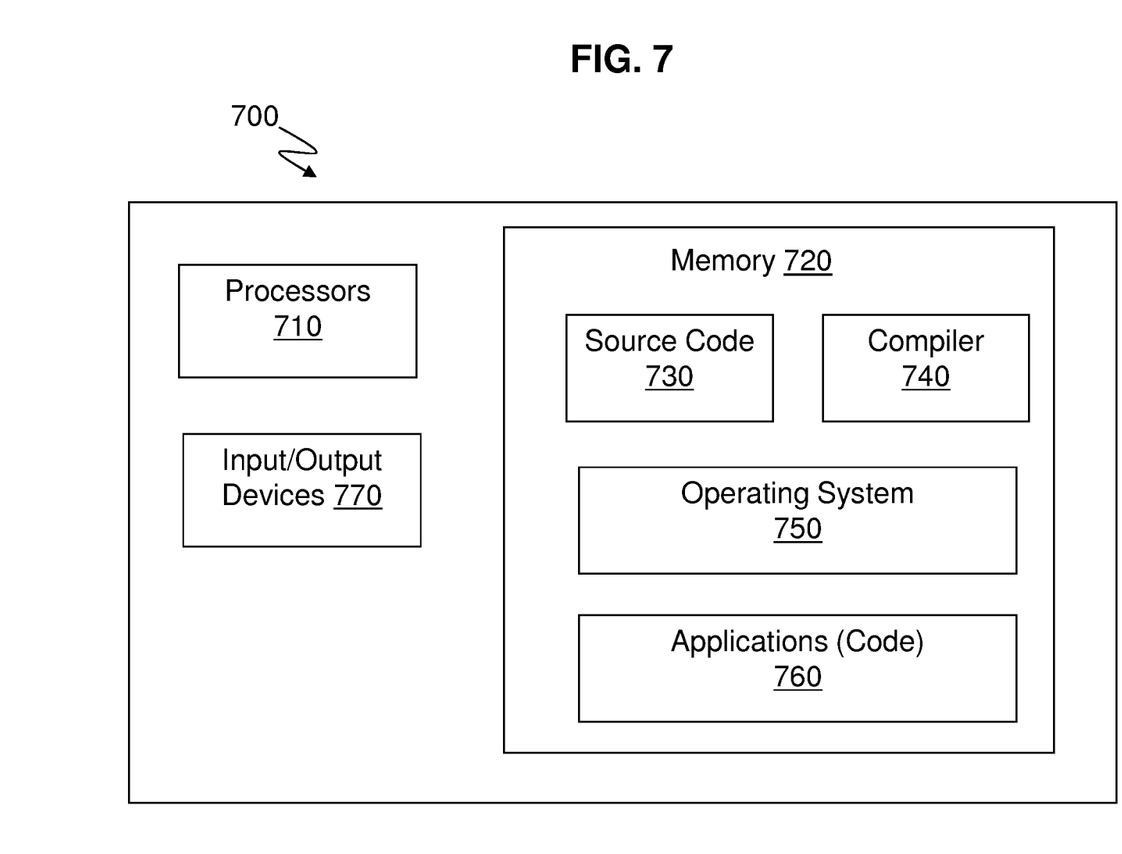
FIG. 7 is a block diagram that illustrates an example of a computer (computer test setup) having capabilities, which may be included in and/or combined with embodiments.

FIG. 7 illustrates an example of a computer 700 (e.g., as part of the computer test setup for testing and analysis) which may implement, control, and/or regulate the voltage of the voltage source 106, and measurements of the ammeters 160 and 165 as discussed herein.

Various methods, procedures, modules, flow diagrams, tools, applications, circuits, elements, and techniques discussed herein may also incorporate and/or utilize the capabilities of the computer 700. Moreover, capabilities of the computer 700 may be utilized to implement features of exemplary embodiments discussed herein. One or more of the capabilities of the computer 700 may be utilized to implement, to connect to, and/or to support any element discussed herein (as understood by one skilled in the art) in FIGS. 1-6. For example, the computer 700 which may be any type of computing device and/or test equipment (including ammeters, voltage sources, connectors, etc.). Input/output device 770 (having proper software and hardware) of computer 700 may include and/or be coupled to the nanodevices and structures discussed herein via cables, plugs, wires, electrodes, patch clamps, etc. Also, the communication interface of the input/output devices 770 comprises hardware and software for communicating with, operatively connecting to, reading, and/or controlling voltage sources, ammeters, and current traces (e.g., magnitude and time duration of current), etc., as discussed herein. The user interfaces of the input/output device 770 may include, e.g., a track ball, mouse, pointing device, keyboard, touch screen, etc., for interacting with the computer 700, such as inputting information, making selections, independently controlling different voltages sources, and/or displaying, viewing and recording current traces for each base, molecule, biomolecules, etc.

Generally, in terms of hardware architecture, the computer 700 may include one or more processors 710, computer readable storage memory 720, and one or more input and/or output (I/O) devices 770 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 710 is a hardware device for executing software that can be stored in the memory 720. The processor 710 can be virtually any custom made or commercially available processor, a central processing unit (CPU), a data signal processor (DSP), or an auxiliary processor among several processors associated with the computer 700, and the processor 710 may be a semiconductor based microprocessor (in the form of a microchip) or a macroprocessor.

The computer readable memory 720 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 720 may incorporate electronic, magnetic, optical, and/or other types of storage media. Note that the memory 720 can have a distributed architecture, where various components are situated remote from one another, but can be accessed by the processor 710.

The software in the computer readable memory 720 may include one or more separate programs, each of which comprises an ordered listing of executable instructions for implementing logical functions. The software in the memory 720 includes a suitable operating system (O/S) 750, compiler 740, source code 730, and one or more applications 760 of the exemplary embodiments. As illustrated, the application 760 comprises numerous functional components for implementing the features, processes, methods, functions, and operations of the exemplary embodiments.

The operating system 750 may control the execution of other computer programs, and provides scheduling, input-output control, file and data management, memory management, and communication control and related services.

The application 760 may be a source program, executable program (object code), script, or any other entity comprising a set of instructions to be performed. When a source program, then the program is usually translated via a compiler (such as the compiler 740), assembler, interpreter, or the like, which may or may not be included within the memory 720, so as to operate properly in connection with the O/S 750. Furthermore, the application 760 can be written as (a) an object oriented programming language, which has classes of data and methods, or (b) a procedure programming language, which has routines, subroutines, and/or functions.

The I/O devices 770 may include input devices (or peripherals) such as, for example but not limited to, a mouse, keyboard, scanner, microphone, camera, etc. Furthermore, the I/O devices 770 may also include output devices (or peripherals), for example but not limited to, a printer, display, etc. Finally, the I/O devices 770 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 770 also include components for communicating over various networks, such as the Internet or an intranet. The I/O devices 770 may be connected to and/or communicate with the processor 710 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 760 is implemented in hardware, the application 760 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A method for ratcheting a double strand molecule, the method comprising:
    driving the double strand molecule into a first Y-channel and a second Y-channel of a membrane by a first voltage pulse, the first Y-channel includes a first stem and first branches, the first branches being connected to the first stem at a first junction;
    wherein the second Y-channel includes a second stem and second branches formed in the membrane, the second branches being connected to the second stem at a second junction, wherein at least one of the second branches of the second Y-channel is connected to at least one of the first branches of the first Y-channel such that one or more of the first branches feeds into the second Y-channel;
    slowing the double strand molecule at the first junction of the first Y-channel based on the first voltage pulse being weaker than a force required to break a base pair of the double strand molecule;
    splitting the double strand molecule into a first single strand and a second single strand by driving the double strand molecule into the first junction of the first Y-channel at a second voltage pulse; and
    reversing a direction of the double strand molecule through the membrane by discontinuing the first voltage pulse and the second voltage pulse.

2. The method of claim 1, wherein the double strand molecule is deoxyribonucleic acid or ribonucleic acid.

3. The method of claim 1, wherein the membrane comprises three or more Y-channels, each having its stem and corresponding branches.

4. The method of claim 1, wherein the Y-channel is a Y-shaped carbon nanotube.

5. The method of claim 1, further comprising alternatingly applying the first voltage pulse for a first time period and the second voltage pulse for a second time period until the double strand molecule has been completely split into the first single strand and the second single strand.

* * * * *